United States Patent [19]

Weigert

[11] Patent Number: 4,910,351

[45] Date of Patent: Mar. 20, 1990

[54] PROCESS FOR PREPARING (POLYFLUOROALKYL)POLYFLUOROARENES

[75] Inventor: Frank J. Weigert, Wilmington, Del.

[73] Assignee: E. I. Du Pont de Nemours and Company, Wilmington, Del.

[21] Appl. No.: 26,538

[22] Filed: Mar. 16, 1987

[51] Int. Cl.$^4$ .................. C07C 17/26; C07C 17/32; C07C 21/24; C07D 211/72

[52] U.S. Cl. .................................... 570/144; 546/345; 558/359

[58] Field of Search ................. 570/144; 546/545; 558/559

[56] References Cited

U.S. PATENT DOCUMENTS 3,318,963  5/1967  Pass ..................................... 570/144
3,408,411  10/1968  McLoughlin et al. ............. 570/144

FOREIGN PATENT DOCUMENTS 026876  2/1981  Japan .
1156912  7/1969  United Kingdom ................ 570/144
1416181  12/1975  United Kingdom ................ 570/144

OTHER PUBLICATIONS

McLoughlin et al., Tetrahedron, 25:5921, (1961).
Pass, J. Chem. Soc., 824, (1965).

Primary Examiner—J. E. Evans

[57] ABSTRACT

A process for preparing (polyfluoroalkyl)polyfluoroarenes comprising contacting a polyfluoroalkyl or perfluoroalkylene of specified formulae with a polyfluoroaromatic in the presence of at least one specified metal reagent is disclosed.

21 Claims, No Drawings

PROCESS FOR PREPARING (POLYFLUOROALKYL)POLYFLUOROARENES

BACKGROUND OF THE INVENTION

1. Field of the Invention

The present invention concerns a process for preparing (polyfluoroalkyl)polyfluoroarenes.

2. Background of the Invention (Polyfluoroalkyl)polyfluoroarenes are useful as intermediates for high temperature solvents, synthetic oxygen carriers, solder masks and other chemical syntheses. Typically, these compounds are prepared by exhaustive fluorination of the corresponding hydrocarbons by either electrochemical techniques or reactions with $CoF_3$. One problem associated with these techniques or reactions is the presence of residual hydrogen in the resulting compositions. It has been found that residual hydrogen adversely affects the stability of the compounds in critical applications such as high temperature solvents and synthetic oxygen carriers. Improved processes for preparing these compounds are of interest to the chemical industry.

Japanese Patent JP-026876 discloses the preparation of perfluoroalkyl benzene derivatives from benzene derivatives, metallic copper, and perfluoroalkyl iodide. The benzene derivatives have the formula $C_6H_4R^1R^2$ wherein $R^1$ and $R^2$ are H, halogen, alkyl, substituted alkyl, amino, amido, carboxyl, alkoxycarbonyl, hydroxyl, alkoxy, substituted alkoxy, aryloxy, acyl, acyloxy, aryl or cyano. The products have the formula $C_6H_3R^1R^2R_f$ wherein $R^1$ and $R^2$ are as defined above and $R_f$ is a perfluoroalkyl group containing from 1 to 7 carbon atoms.

McLoughlin et al., *Tetrahedron*, 25: 5921 (1961) discloses that iodofluoroalkanes and iodoaromatic compounds react with copper in polar aprotic solvents to give (fluoroalkyl) aromatic compounds. The reference discloses that the iodofluoroalkanes and iodoaromatic compounds can bear a wide variety of substituents (carboxyl, nitro, amino, hydroxyl, etc.). In one reaction, $C_6F_5C_7F_{15}$ is prepared by reacting $C_7F_{15}I$, $C_6F_5Br$ and $Cu°$ at 120° C. In another reaction, $C_6F_5(CF_2)_3C_6F_5$ is prepared by reacting $C_6F_5Br$, $I(CF_2)_2I$ and $Cu°$ at 120° C. These reactions were conducted in the presence of polar aprotic solvents.

Pass, *J. Chem. Soc.*, 824 (1965) discloses dehydrochlorination reactions involving trifluoromethane. In one reaction, $C_6F_5CF_3$ is prepared by reacting $C_6F_5Cl$ with $CF_3H$ at 700° for 10 seconds in a nickel tube.

SUMMARY OF THE INVENTION

The present invention provides a process for preparing (polyfluoroalkyl)polyfluoroarenes comprising contacting at least one polyfluoroalkyl of the formula, $C_xF_{2x+1}Z$, or at least one perfluoroalkylene of the formula, $Z(CF_2)_yZ$, with a polyfluoroaromatic of the formula, ArDB, in the presence of at least one metal reagent selected from the group consisting of Cu, Zn, Ni, Ag, Sn, and Ca, wherein the formulas:

D is F, Cl, Br, or I;

B is F, Cl, Br, I, H, CN, or $C_nF_{2n+1}$, wherein n is an integer from 1 to 10, inclusive, and provided that n and x, independently, are 1 to 3 when the process is vapor phase;

Z is, independently, Cl, Br, I, or H;

Ar is $C_6F_4$, $C_5F_3N$, $C_{10}F_6$ or $C_{12}F_8$;

x is an integer from 1 to 7, inclusive;

y is an integer from 3 to 6, inclusive.

DETAILED DESCRIPTION OF THE INVENTION

The present invention provides a process for preparing (polyfluoroalkyl)polyfluoroarenes. As used herein the expression "(polyfluoroalkyl)polyfluoroarenes" means compounds having the formula $C_xF_{2x+1}ArB$ or $ArBC_xF_{2x}ArB$ wherein x, Ar, and B are as defined above. The process comprises contacting at least one polyfluoroalkyl or perfluoroalkylene with a polyfluoroaromatic in the presence of a metal reagent. Suitably polyfluoroalkyls and perfluoroalkylenes are of the formulae, $C_xF_{2x+1}Z$ and $Z(CF_2)_yZ$, respectively, wherein x, y and Z are as defined above. Preferably x is 1; D is I or F; and Z is I or Br. The fluoroaromatic is of the formula, ArDB, wherein Ar, D and B, and preferred embodiments of D, are as defined above. Preferably, Ar is $C_6F_4$. These starting materials are well known in the art.

The process can be conducted in a batch or continuous mode. In a preferred embodiment, the metal reagent is is at least one selected from the group consisting of Cu and Zn, and most preferably the metal reagent is Cu. The process can be conducted in the vapor phase or the liquid phase, and preferably the liquid phase is run neat. The process can be conducted at a temperature of from about 150° C. to about 700° C. When the process is conducted in the vapor phase, preferred reaction temperatures are from about 350° C. to about 700° C. For liquid phase processes preferred reaction temperatures are from about 150° C. to about 350° C. Preferably, the contact time of the reactants with the metal reagent is from about 0.1 to about 10 seconds for vapor phase reactions and from about 1 to about 48 hours for liquid phase reactions. Preferably the process is conducted at a pressure of from about 0.001 MPa (0.01 atm) to about 10 MPa (100 atm). In a preferred vapor phase reaction, the reaction temperature is from about 350° C. to about 400° C., the metal reagent is Zn, Z is I, and D is I.

The invention is further described by the following examples wherein all parts and percentages are by weight and degrees are Celsius, unless otherwise stated.

EXAMPLE 1

A 10 cm glass reactor having a diameter of 1 cm was charged with 5 g of a metal reagent containing 80% CuO and 20% $Cr_2O_3$. The reactor was heated in a tube furnace at 600°. Feed streams of $C_6F_6$ and $CF_3I$ were passed through the reactor at rates of 1 mL/hr and 5 mL/min, respectively, and the resulting reactor effluent was condensed at −78°. The resulting product was analyzed and found to contain 72% $C_6F_6$ and 16% $C_6F_5CF_3$.

EXAMPLES 2–10

The procedure described in Example 1 was substantially repeated nine times employing the metal reagent, reaction temperatures and feed streams of $C_6F_6$ and $CF_3Br$ described in Table 1. The results are set forth in Table 1.

TABLE 1

| Ex | Reagent | Temp.(°) | Feed rate C$_6$F$_6$(mL/hr) | CF$_3$Br(mL/min) | Product Composition |
|----|---------|----------|-----------------------------|------------------|---------------------|
| 2  | 5 g of A  | 600 | 1   | 5  | 53% C$_6$F$_6$, 37% C$_6$F$_5$CF$_3$ |
| 3  | 29 g of B | 600 | 1   | 5  | 46% C$_6$F$_6$, 49% C$_6$F$_5$CF$_3$ |
| 4  | 5 g of C  | 400 | 1   | 5  | 78% C$_6$F$_6$, 17% C$_6$F$_5$CF$_3$ |
| 5  | 5 g of D  | 600 | 1   | 5  | 79% C$_6$F$_6$, 16% C$_6$F$_5$CF$_3$ |
| 6  | 29 g of B | 600 | 0.5 | 3  | 36% C$_6$F$_6$, 51% C$_6$F$_5$CF$_3$ 9% C$_6$F$_4$(CF$_3$)$_2$ |
| 7  | 29 g of B | 650 | 0.5 | 3  | 17% C$_6$F$_6$, 56% C$_6$F$_5$CF$_3$ 20% C$_6$F$_4$(CF$_3$)$_2$ |
| 8  | 29 g of B | 650 | 0.5 | 10 | 15% C$_6$F$_6$, 57% C$_6$F$_5$CF$_3$ 23% C$_6$F$_4$(CF$_3$)$_2$ |
| 9  | 5 g of E  | 600 | 1   | 5  | 83% C$_6$F$_6$, 13% C$_6$F$_5$CF$_3$ |
| 10 | 5 g of F  | 600 | 1   | 5  | 84% C$_6$F$_6$, 14% C$_6$F$_5$CF$_3$ |

COMPOSITIONS
A = 80% CuO/20% Cr$_2$O$_3$
B = Cu shot
C = Zn
D = Ni
E = Ag
F = Ca

EXAMPLE 11

The procedure described in Example 1 was substantially repeated except that feed streams of C$_6$F$_6$ and CF$_3$H were passed through the reactor at rates of 1 mL/hr and 5 mL/min, respectively. The resulting product contained 34% C$_6$F$_6$ and 44% C$_6$F$_5$CF$_3$.

EXAMPLE 12

The procedure described in Example 1 was substantially repeated except that feed streams of C$_6$F$_5$CN and CF$_3$Br were passed through the reactor at rates of 1 mL/hr and 5 mL/min, respectively. The resulting product contained 65% C$_6$F$_5$CN and 35% CF$_3$C$_6$F$_4$CN (equal amounts of o, m, and p).

EXAMPLE 13

The procedure described in Example 1 was substantially repeated except that 10 g of the reagent were employed, the reaction temperature was 650°, and feed streams of C$_5$F$_5$N and CF$_3$Br were passed through the reactor at rates of 1 mL/hr and 5 mL/min, respectively. The resulting product contained 73% C$_5$F$_5$N and 27% C$_5$F$_4$NCF$_3$ (78% 3−, 8% 2−, 14% 4−).

EXAMPLE 14

The procedure described in Example 1 was substantially repeated except that 5 g of Zn/SiC catalyst were employed, the reaction temperature was 400°, and feed streams of C$_6$F$_5$Br/C$_6$F$_6$ (1:3 v/v) and CF$_3$I were passed through the reactor at rates of 1 mL/hr and 5 mL/min, respectively. The resulting product contained 77% C$_6$F$_6$ and 15% C$_6$F$_5$CF$_3$. All of the C$_6$F$_5$Br was consumed.

EXAMPLE 15

The procedure described in Example 1 was substantially repeated except that the reaction temperature was 500° and feed streams of C$_6$F$_5$I and CF$_3$Br were passed through the reactor at rates of 1 mL/hr and 5 mL/min, respectively. The resulting product contained 60% C$_6$F$_5$I and 7% CF$_3$C$_6$F$_5$.

EXAMPLE 16

The procedure described in Example 1 was substantially repeated except that the metal reagent was 9 g of Zn-SiC, the reaction temperature was 500°, and feed streams of C$_6$F$_5$Br and n-C$_3$F$_7$Br were passed through the reactor at rates of 1 mL/hr and 5 mL/min, respectively.

The resulting product contained 61% C$_6$F$_{14}$, 19% C$_6$F$_5$H, 10% C$_6$F$_5$C$_3$F$_7$, 2% C$_6$F$_5$Br, and 5% C$_6$F$_5$C$_6$F$_5$.

EXAMPLE 17-20

The procedure described in Example 1 was substantially repeated four times except that the reaction temperatures and feed streams shown in Table 2 were employed. The results are shown in Table 2.

TABLE 2

| Ex. | Temp.(°) | Feed Stream A (rate) | Feed Stream B (rate) | Product Composition |
|-----|----------|----------------------|----------------------|---------------------|
| 17 | 600 | C$_{10}$F$_8$ (1 mL/hr) | CF$_3$Br (5 mL/min) | 32% C$_{10}$F$_8$, 59% composed of C$_{10}$F$_7$CF$_3$, C$_{10}$F$_6$(CF$_3$)$_2$, C$_{10}$F$_5$(CF$_3$)$_3$ |
| 18 | 650 | C$_{12}$F$_{10}$ (1 mL/hr) | CF$_3$Br (5 mL/min) | 38% C$_{12}$F$_{10}$, 38% composed of C$_{12}$F$_9$CF$_3$, C$_{12}$F$_8$(CF$_3$)$_2$, C$_{12}$F$_7$(CF$_3$)$_3$ |
| 19 | 650 | C$_6$F$_5$Cl (1 mL/hr) | CF$_3$H (5 mL/min) | 29% C$_6$F$_5$Cl, 19% C$_6$F$_5$CF$_3$ |
| 20 | 450 | C$_6$F$_5$I (1 mL/hr) | CF$_3$I (5 mL/min) | 36% C$_6$F$_5$I, 37% C$_6$F$_5$CF$_3$, 3% C$_6$F$_5$(CF$_3$)$_2$, 6% C$_6$F$_4$CF$_3$I |

EXAMPLE 21

0.6 g of $C_6F_5I$ and 1.0 g of $C_7F_{15}I$ were reacted in the presence of 1 g of Sn at a temperature of 200° for 18 hours. The resulting reaction mixture was cooled and metal salts were removed. The resulting product contained 53% $C_6F_5I$, 24% $C_7F_{15}I$, and 21% $IC_6F_4C_7F_{15}$.

EXAMPLE 22

The procedure described in Example 21 was substantially repeated except that 1 g of Cu was employed as the metal reagent. The main reaction product was m- and p-$C_6F_5C_6F_4C_7F_{15}$.

EXAMPLE 23

0.5 g of $I(CF_2)_xI$ (68% x=6) and 0.6 g of $C_6F_5I$ were reacted in the presence of 0.5 g of Sn at a temperature of 250° for 8 hours. The resulting reaction mixture was cooled and metal salts were removed. The main reaction products were $C_{22}F_{20}$ and $C_6F_5C_8F_{17}$.

EXAMPLE 24

The procedure described in Example 23 was substantially repeated except that 2 g of Cu was employed as the metal reagent, the reaction temperature was 200°, and the reaction was conducted for 46 hours. The main reaction product was $C_6F_5C_6F_4(CF_2)_6C_6F_4C_6F_5$.

EXAMPLE 25

1 g of $C_7F_{15}I$ and 0.6 g of $C_5F_5N$ were reacted in the presence of 0.7 g of Cu at a temperature of 250° for 4 hours. The resulting reaction mixture was cooled and metal salts were removed. The main reaction product was $C_5F_4NC_7F_{15}$.

What is claimed is:

1. A process for preparing (polyfluoroalkyl)polyfluoroarenes comprising contacting at least one polyfluoroalkyl of the formula, $C_xF_{2x+1}Z$, or at least one perfluoroalkylene of the formula, $Z(CF_2)_yZ$, with a polyfluoroaromatic of the formula, ArDB, in the presence of at least one reagent selected from the group consisting of Cu, Zn, Ni, Ag, Sn, Ca, and CuO mixed with $Cr_2O_3$ wherein the formulas:

D is F, Cl, Br, or I;
B is F, Cl, Br, I, N, CN, or $C_nF_{2n+1}$, wherein n is an integer from 1 to 10, inclusive, and provided that n and x, independently, are 1 to 3 when the process is vapor phase;
Z is, independently, Cl, Br, or I;
Ar is $C_6F_4$, $C_5F_3N$, $C_{10}F_6$ or $C_{12}F_8$;
x is an integer from 1 to 7, inclusive;
y is an integer from 3 to 6, inclusive.

2. A process according to claim 1, wherein the process is conducted in the vapor phase.

3. A process according of claim 2, wherein the reaction temperature is from about 350° C. to about 700° C.

4. A process according to claim 3, wherein the reaction pressure is from about 0.001 MPa to about 10 MPa.

5. A process according to claim 4, wherein the contact time of the reactants with the metal reagent is from about 0.1 to about 10 seconds.

6. A process according to claim 5, wherein the metal reagent is at least one selected from the group consisting of Cu and Zn.

7. A process according to claim 6, wherein the metal reagent is Cu.

8. A process according to claim 6, wherein x is 1.

9. A process according to claim 6, wherein Ar is C6F4.

10. A process according to claim 6, wherein Z is Br.

11. A process according to claim 6, wherein D is F.

12. A process according to claim 6, wherein the metal reagent is Zn, the reaction temperature is from about 350° C. to about 400° C., Z is I, and D is I.

13. A process according to claim 1, wherein the process is conducted in the liquid phase.

14. A process according to claim 13, wherein the reaction temperature is from about 150° C. to about 350° C.

15. A process according to claim 14, wherein the contact time of the reactants with the metal reagent is from about 1 to 48 hours.

16. A process according to claim 15, wherein the metal reagent is at least one selected from the group consisting of Cu and Zn.

17. A process according to claim 16, wherein the liquid phase is run neat.

18. A process according to claim 17, wherein Ar is C6F4.

19. A process according to claim 18, wherein Z is I.

20. A process according to claim 19, wherein D is I.

21. A process according to claim 19, wherein D is F.

* * * * *